(12) United States Patent
Rodemer

(10) Patent No.: US 7,576,642 B2
(45) Date of Patent: Aug. 18, 2009

(54) MOTOR-VEHICLE SEAT BELT WITH INTEGRATED SENSORS

(75) Inventor: Klaus Rodemer, Lautertal (DE)

(73) Assignee: Paragon AG, Dellbruck (DE)

( * ) Notice: Subject to any disclaimer, the term of this patent is extended or adjusted under 35 U.S.C. 154(b) by 806 days.

(21) Appl. No.: 10/556,438

(22) PCT Filed: Apr. 26, 2004

(86) PCT No.: PCT/EP2004/004378

§ 371 (c)(1),
(2), (4) Date: Nov. 10, 2005

(87) PCT Pub. No.: WO2004/110829

PCT Pub. Date: Dec. 23, 2004

(65) Prior Publication Data

US 2006/0250275 A1 Nov. 9, 2006

(30) Foreign Application Priority Data

Jun. 18, 2003 (DE) .................... 103 27 753

(51) Int. Cl.
*B60Q 1/00* (2006.01)
*G08B 23/00* (2006.01)
*G08B 21/00* (2006.01)
*B60R 21/16* (2006.01)
*B60R 22/00* (2006.01)

(52) U.S. Cl. .............. 340/457.1; 340/438; 340/576; 340/667; 340/573.1; 280/735; 280/801.1

(58) Field of Classification Search ............ 340/856.2, 340/856.3, 426.24, 438, 573.1, 576, 667, 340/457.1; 280/735, 801.1
See application file for complete search history.

(56) References Cited

U.S. PATENT DOCUMENTS

| 4,958,853 | A | 9/1990 | Doty |
| 5,060,977 | A | 10/1991 | Saito ........................ 280/802 |
| 5,783,997 | A * | 7/1998 | Saitoh et al. ................ 340/576 |
| 6,195,008 | B1 * | 2/2001 | Bader ...................... 340/573.1 |
| 6,203,059 | B1 * | 3/2001 | Mazur et al. ................ 280/735 |
| 6,441,729 | B1 | 8/2002 | Tu |
| 6,750,764 | B1 * | 6/2004 | Henninger ............... 340/457.1 |

FOREIGN PATENT DOCUMENTS

| DE | EP 0830994 A1 * | 3/1998 |
| DE | 100 26 444 | 5/2000 |
| DE | 100 33 985 | 7/2000 |
| DE | 101 36 267 | 7/2001 |
| DE | 10209695 | 9/2002 |
| JP | 59038153 | 3/1984 |

* cited by examiner

*Primary Examiner*—Benjamin C Lee
*Assistant Examiner*—Lam P Pham
(74) *Attorney, Agent, or Firm*—Andrew Wilford

(57) ABSTRACT

A safety belt has an inner face turned toward the body of a user and an outer face turned away from the user. A plurality of sensor are mounted on the outer face, and the inner face is devoid of sensors. A selector connected to the sensors determines which sensor is best positioned for signal quality and for using the signal therefrom.

21 Claims, 1 Drawing Sheet

MOTOR-VEHICLE SEAT BELT WITH INTEGRATED SENSORS

CROSS REFERENCE TO RELATED APPLICATIONS

This application is the US national phase of PCT application PCT/EP2004/004378, filed 26 Apr. 2004, published 23 Dec. 2004 as WO2004/110829, and claiming the priority of German patent application 10327753.6 itself filed 18 Jun. 2003, whose entire disclosures are herewith incorporated by reference.

FIELD OF THE INVENTION

The invention relates to a sensor arrangement for attaching to a belt, in particular to a motor vehicle safety belt.

BACKGROUND OF THE INVENTION

With such sensor arrangements know from the prior art the sensors are arranged on the safety belt or are attached thereto, in that for example fittings penetrating the safety belt or the like are provided. Common to all known fittings or attachments of the sensors on the safety belt is that on the one hand the mechanical properties of the belt are impaired, whereby furthermore the support properties of the safety belt are changed negatively insofar as the smooth structure of the inner face of the belt facing the occupants of the vehicle is disturbed by elements of the fittings or attachments projecting on the inner face of the safety belt. This smooth structure of the inner face of the belt is however of major significance to ensure the necessary easy-running gliding of the safety belt over the deflection elements of the safety belt arrangements and the body of the vehicle occupants. The result of any impairment to these glide properties of the safety belt can be that the safety belt is no longer tightened optimally on the body of the vehicle occupants by the retractors of the safety belt arrangement following movements of the occupants of the vehicle.

In the event of a possible accident or the like the safety belt would thus deploy its protective function inadequately only, if at all.

OBJECT OF THE INVENTION

The object of the invention is to provide a sensor arrangement for applying to a belt, in particular on a safety belt of a motor vehicle, which results in no or little impairing of the glide properties on the inner face of same essential for the protective function of the safety belt.

SUMMARY OF THE INVENTION

This object is attained according to the present invention by at least one, preferably each sensor of the sensor arrangement being arranged on the outer face of the safety belt facing away from the body of the vehicle occupants, whereby the inner face of the safety belt facing the body of the vehicle occupants remains free and unchanged.

Such applying or fixing of the sensors of the sensor arrangement on the belt can be achieved if at least one sensor is taken up on a fitting or in a housing, which can be fastened on the outer face of the safety belt.

The housing can be made advantageously from plastic.

The housing can be attached to the outer face of the safety belt by welding with the material forming the outer face of the safety belt or by adhesion on the outer face of the safety belt.

It is also possible to sew the housing of at least one sensor on the outer face of the safety belt.

To prevent the safety belt from being partly weakened in those areas where the sensors of the sensor arrangement are provided, it is appropriate to reinforce the safety belt in these areas by weaving in additional threads.

Alternatively, the belt can be reinforced in the areas with the sensors of the sensor arrangement of the safety belt by adding in threads in these areas with better mechanical properties, e.g. increased breaking load and/or elasticity, for physically forming the safety belt.

The sensors of the sensor arrangement can be designed e.g. as microphones. It is then possible, without the interference of hand grips, which might hinder proper control of the vehicle, to comfortably make a selection.

Alternatively or additionally, sensors designed as heart frequency, body temperature meters or the like can be provided. In the event of a signal from a heart frequency meter, which whether the vehicle driver is competent to drive, operation of the vehicle can be taken over for example such that as far as possible no or minimal damage will result.

The sensors of the sensor arrangement are appropriately connected to conductors integrated in the safety belt, into which or from which the required operating energy of the sensor arrangement and signals of the sensors can be inductively coupled or uncoupled. The sensors of the sensor arrangement can be attached in different topologies. This depends on the structural type of the sensors. Sensors, which deliver an adequate signal value, are contacted individually or with a common reference conductor. Sensors with low signal value frequently require a separate voltage supply. Integrated sensors can be connected together to a common bus.

The operating power and the signals can advantageously be coupled or uncoupled in the region of one of two retractors or a belt lock of the safety belt arrangement.

With respect to their breaking and expansion properties, conductors woven into the safety belt have particularly advantageous properties, if the conductors are woven right in as the original filament of the safety belt. The angle and spacing of the conductors during weaving then determine the expansion behavior. In addition, the conductors in this advantageous embodiment of the invention are not visible from outside.

The connection between the sensors on the one hand and the conductors integrated into the safety belt on the other hand can advantageously be effected by means of flexiconductors or conductive elastomers.

In order to determine the sensor of the sensor arrangement best positioned for the respective purpose, it is advantageous if a selection device is provided by means of which the sensor of the sensor arrangement best positioned for the signal quality can be determined, whereby the signal of this sensor can then be selected for forwarding.

To further improve the output signal the selection device should select the two sensors of the sensor arrangement best positioned for signal quality, e.g. the first sensor arranged above and the first sensor arranged below the signal source, and should form the output signal of the sensor arrangement from the signals of both these sensors. The signals of the sensors can be processed by amplifying and standardizing the signals, but also with linearizing and filtering of the signals. The best positioned sensor or the best-positioned sensor group can be selected by signal-evaluation without consideration for the belt length or the seated position by means of the selection device.

The output signal of the selected sensor or selected sensor group including the signals of the other sensors of the sensor arrangement can be processed preferably according to any mathematical method, with the possibility for example of filtering out wind noise, e.g. in a convertible, from a microphone signal.

The selection device can operate in view of the output signals from a seated position sensor and/or a sensor for the weight of occupants of the vehicle and/or a safety belt length of stretch sensor, and independently make the selection of the best-positioned sensors.

BRIEF DESCRIPTION OF THE DRAWING

The invention will now be explained in greater detail hereinbelow by means of an embodiment with reference to the diagram, in which.

SPECIFIC DESCRIPTION

Figure 1:
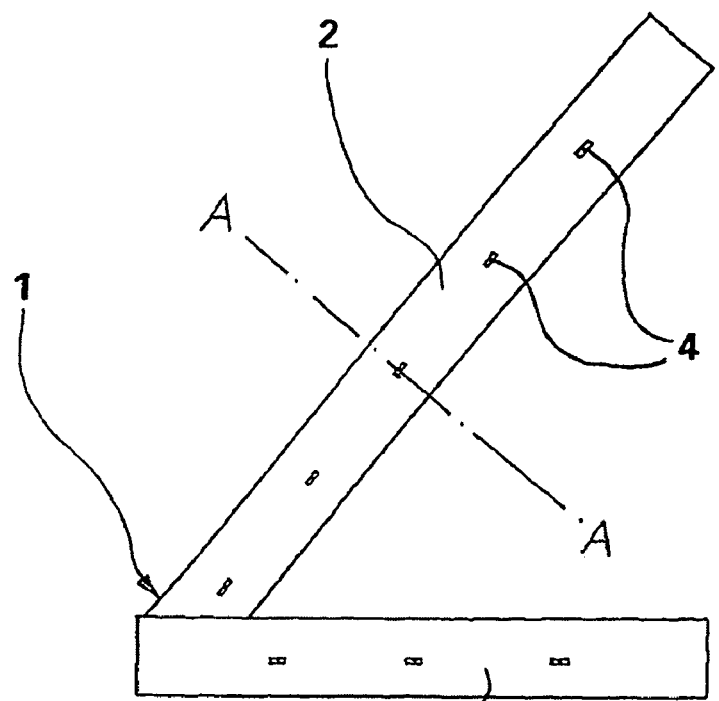
FIG. 1 is a basic illustration of a safety belt fitted with a sensor arrangement according to the present invention.

A safety belt 1 shown in a basic illustration in FIG. 1 is subdivided into a shoulder belt part 2 running obliquely upward and a lap belt part 3 running approximately horizontally.

A sensor arrangement is provided on the front side of the safety belt 1 visible in FIG. 1 and turned away from the body of a person protected by the safety belt 1, to which a plurality of sensors 4 belongs. In the illustrated embodiment the sensors 4 of the sensor arrangement are arranged at approximately the same spacing in a longitudinal direction both of the shoulder belt part 2 and also of the lap belt part 3.

As already explained, the sensors 4 sit on the outer face 5 of the safety belt 1 facing away from the vehicle occupants.

The inner face 6 of the safety belt 1 is not impaired by the sensors 4 of the sensor arrangement and is fully undisturbed. The run of the safety belt 1 in deflection elements and the like is thus not hindered by the sensors 4 of the sensor arrangement.

In the illustrated embodiment each sensor 4 of the sensor arrangement has a housing 7 in which it is received and by means of which it is mounted on the outer face 5 of the safety belt 1. Depending on the physical form of the sensor 4 it is also possible to arrange the latter not by means of a housing 7 but by means of another kind of fitting on the outer face 5 of the safety belt 1.

Figure 2:
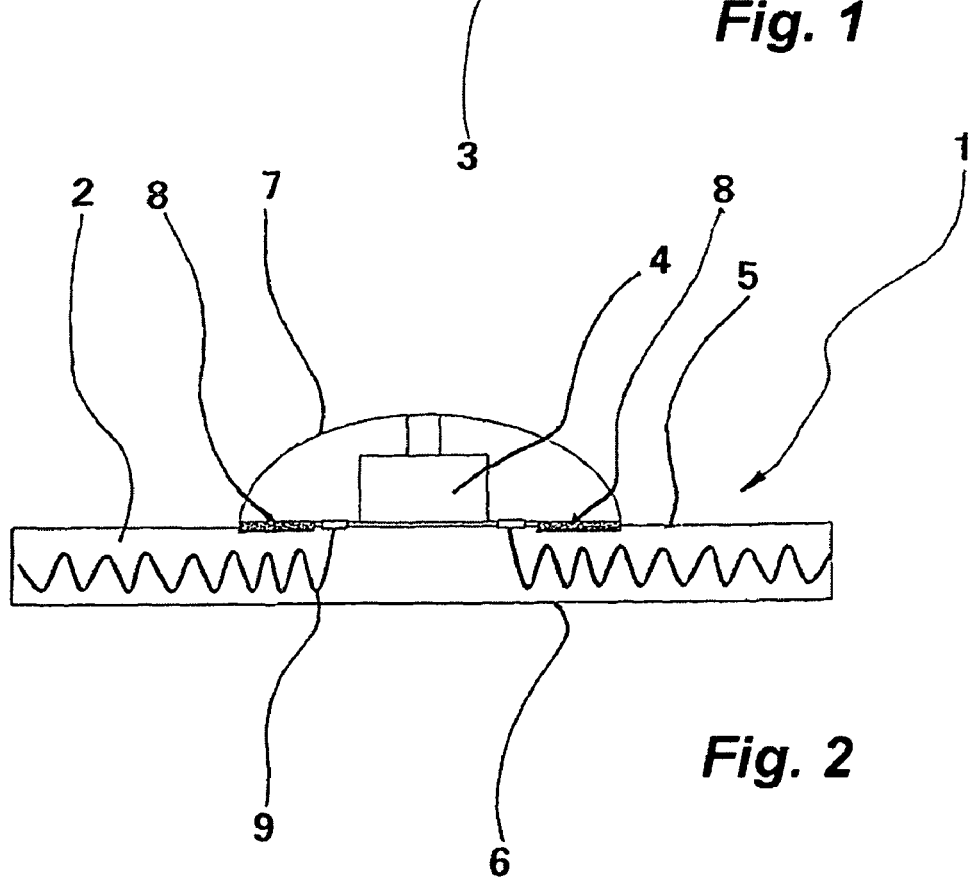
FIG. 2 illustrates section A-A in FIG. 1.

As best evident from FIG. 2, the housing 7 containing the sensor 4 is connected by means of a connection 8 solidly to the material forming the outer face 5 of the safety belt 1. The connection 8 can be a weld joint, an adhesive joint and also a seam or the like.

The safety belt 1 can be strengthened by means of woven-in threads at those points, at which the sensors 4 of the sensor arrangement are provided, to balance out any possible weaknesses of the safety belt 1, occurring due to the mounting of the sensors 4.

The sensors 4 illustrated in FIG. 1 or 2 can be for example microphones, which it is possible for the occupant of the vehicle to use without having to manipulate any distracting hand grips impairing his concentration on controlling the vehicle. Of course, the sensor arrangement formed by the sensors 4 can be provided on every safety belt inside the vehicle.

Alternatively or in addition to this, sensors 4 designed as heart frequency and body temperature sensors or the like can be provided.

In the embodiment illustrated in the figures conductors 9 are integrated in the safety belt 1 for power supply and for signal connection of the sensors 4. The required operating energy can be fed to the sensors 4 by means of these conductors 9, whereby the signal output from the sensors 4 can take place by means of the conductors 9 also.

Both coupling of the operating power required for operating the sensors 4 and also uncoupling the signals from the sensors 4 can be carried out inductively, whereby one of two retractors of the safety belt 1 can serve as coupling or uncoupling point.

The conductors 9 integrated in the safety belt 1 can be spun about web filaments of the safety belt 1.

The connection between the conductors 9 on the one hand and the sensors 4 on the other hand can be realized by means of flexiconductors, conductive elastomers and the like.

The sensor arrangement formed by the sensors 4 includes a selection device not shown in FIGS. 1 and 2, which receives signals from all sensors 4 of the sensor arrangement. The signal quality of the individual sensors 4 can be established in the selection device not shown in the figures. It is possible, by means of the selection device, to select a particular sensor or two sensors 4 whose signal quality is best. As long as both sensors 4 with the best signal quality are selected, their signals can be combined into one output signal.

Also, it is possible to refine this output signal further, in that the signals of the sensors 4 not selected for combining the output signal are considered and employed for processing the output signal.

One seated position sensor and one sensor for the weight of the occupants of the vehicle can be connected to the selection device. Its output signals can be used in selection of the sensors 4 of the sensor arrangement best positioned for signal quality, whereby the output signal of a safety belt length of stretch sensor can be considered for this selection also.

The invention claimed is:

1. In a motor-vehicle safety belt having an inner face turned toward the body of a user and an outer face turned away from the user, a sensor arrangement comprising:

at least one sensor on the outer face to detect one or more parameters of the user, the inner face being devoid of any sensor;

the belt being reinforced at least adjacent the at least one sensor with filaments of greater strength than filaments otherwise forming the belt.

2. The sensor arrangement as claimed in claim 1 wherein the sensor is contained a fitting or housing fastened to the outer face of the safety belt.

3. The sensor arrangement as claimed in claim 2 wherein the housing of is made of plastic.

4. The sensor arrangement as claimed in claim 2 wherein the housing is welded to material forming the outer face of the safety belt.

5. The sensor arrangement as claimed in claim 2 wherein the housing is adhered to material forming the outer face of the safety belt.

6. The sensor arrangement as claimed in claim 2 wherein the housing is sewn to the outer face (5) of the safety belt.

7. In a motor-vehicle safety belt having an inner face turned toward the body of a user and an outer face turned away from the user, a sensor arrangement comprising:

at least one sensor on the outer face to detect one or more parameters of the user, the inner face being devoid of any sensor; and conductors integrated into the belt and connected to the at least one sensor and detection circuitry.

8. The sensor arrangement as claimed in claim 7 wherein the safety belt is provided in the region of the sensor with belt reinforcing.

9. The sensor arrangement as claimed in claim 8 wherein the belt reinforcing is filaments additionally woven into the safety belt.

10. The sensor arrangement as claimed in claim 8 wherein the belt reinforcing is filaments with better mechanical properties.

11. The sensor arrangement as claimed in claim 7 wherein the operating energy and signal of the at least one sensor can be coupled or uncoupled in the region of one of two retractors or a belt lock of the safety belt.

12. The sensor arrangement as claimed in claim 7 wherein the conductors integrated in the safety belt are woven with filaments of the safety belt.

13. In a motor-vehicle safety belt having an inner face turned toward the body of a user and an outer face turned away from the user, a sensor arrangement comprising:

a plurality of sensors on the outer face to detect one or more parameters of the user, the inner face being devoid of any sensor; and selector means for determining which sensor is best positioned for signal quality and for using the signal therefrom.

14. The sensor arrangement as claimed in claim 13 wherein there are a plurality of the sensors that are each arranged on the outer face of the safety belt facing away from the body of the vehicle occupants, the inner face of the safety belt facing the body of the vehicle occupants being free and unchanged.

15. The sensor arrangement as claimed in claim 13 wherein the sensors are microphones.

16. The sensor arrangement as claimed in claim 13 wherein the sensors detect heart frequency or body temperature.

17. The sensor arrangement as claimed in claim 13 wherein the sensors are connected by means of flexiconductors to the conductors integrated in the safety belt.

18. The sensor arrangement as claimed in claim 17 wherein the sensors are connected by means of conductive elastomers to the conductors integrated in the safety belt.

19. The sensor arrangement as claimed in claim 13 wherein by means of the selector means the two sensors of the sensor arrangement best positioned for signal quality can be determined and the signals of both these sensors can be combined into one output signal.

20. The sensor arrangement as claimed in claim 13 wherein an output signal of the selected sensor or an output signal combined from the signals of two or more selected sensors along with the signals of the other sensors of the sensor arrangement can be processed preferably according to any mathematical method.

21. The sensor arrangement as claimed in claim 13 wherein the selector means is connected to a seated position sensor or a sensor for weight of the occupants of the vehicle, whereby the output signals of this or respectively of these sensors can be viewed together with an output signal of a safety belt length of stretch sensor in selection of the best-positioned sensors of the sensor arrangement.

\* \* \* \* \*